(12) United States Patent
McGeer et al.

(10) Patent No.: US 11,013,750 B2
(45) Date of Patent: May 25, 2021

(54) METHODS FOR TREATING AND PREVENTING NOCICEPTIVE PAIN

(71) Applicant: Aurin Biotech Inc., Vancouver (CA)

(72) Inventors: Patrick L. McGeer, Vancouver (CA); Moonhee Lee, Vancouver (CA); Krista Kennedy, North Vancouver (CA); Edith G. McGeer, Vancouver (CA); Douglas N. Bell, Rancho Mirage, CA (US)

(73) Assignee: Aurin Biotech Inc., Vancouver (CA)

( * ) Notice: Subject to any disclaimer, the term of this patent is extended or adjusted under 35 U.S.C. 154(b) by 60 days.

(21) Appl. No.: 15/411,438

(22) Filed: Jan. 20, 2017

(65) Prior Publication Data

US 2018/0207180 A1    Jul. 26, 2018

(51) Int. Cl.
*A61K 31/616*  (2006.01)
*A61K 9/00*  (2006.01)
*A61K 9/06*  (2006.01)
*A61K 9/08*  (2006.01)
*A61K 31/603*  (2006.01)

(52) U.S. Cl.
CPC .......... *A61K 31/616* (2013.01); *A61K 9/0014* (2013.01); *A61K 9/06* (2013.01); *A61K 9/08* (2013.01); *A61K 31/603* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 1,743,630 A | 1/1930 | Summers | |
| 1,764,035 A | 6/1930 | Summers | |
| 4,002,745 A | 1/1977 | Bernstein et al. | |
| 4,007,270 A | 2/1977 | Bernstein | |
| 6,538,028 B1 | 3/2003 | Pierson, III et al. | |
| 8,877,808 B2 | 11/2014 | McGeer | |
| 2003/0104976 A1* | 6/2003 | Davar | A61P 29/00 514/1 |
| 2004/0072785 A1* | 4/2004 | Wolff | A61K 31/7088 514/44 A |

(Continued)

FOREIGN PATENT DOCUMENTS

| CN | 102659844 A | 9/2012 |
|---|---|---|
| WO | 9929706 A2 | 6/1999 |

(Continued)

OTHER PUBLICATIONS

"Aurintricarboxylic acid", Product Information, Sigma-Aldrich (Mar. 2003).*

(Continued)

*Primary Examiner* — Bethany P Barham
*Assistant Examiner* — Barbara S Frazier
(74) *Attorney, Agent, or Firm* — Oyen Wiggs Green & Mutala LLP (57) ABSTRACT

Methods of treating a condition resulting in nociceptive pain are provided. The method includes the step of administering to a mammal a therapeutically effective amount of a compound selected from the group consisting of diacetyl salicylic acid (DAS), aurin tricarboxylic acid (ATA), aurin quadracarboxylic acid (AQA), aurin hexacarboxylic acid (AHA), and/or a combination thereof.

7 Claims, 8 Drawing Sheets

(56) References Cited

U.S. PATENT DOCUMENTS

| | | | |
|---|---|---|---|
| 2010/0239632 A1* | 9/2010 | Walsh | A61K 9/0024 424/423 |
| 2013/0035388 A1 | 2/2013 | McGeer | |
| 2015/0065573 A1 | 3/2015 | McGeer | |

FOREIGN PATENT DOCUMENTS

| | | |
|---|---|---|
| WO | 0112202 A2 | 2/2001 |
| WO | 13155047 A2 | 10/2013 |
| WO | 2014085920 A1 | 6/2014 |
| WO | 15070354 A1 | 5/2015 |
| WO | 2015070354 A1 | 5/2015 |

OTHER PUBLICATIONS

Cushman, Mark and Suseela Kanamatharaeddy, "Synthesis of the covalent hydrate of the incorrectly assumed structure of aurintricarboxylic acid (ATA)", Tetrahedron, 1990, 46(5):1491-1498.

Cushman, Mark, et al, "Synthesis and anti-HIV activities of low molecular weight aurintricarboxylic acid fragments and related compounds", J Med Chem, 1991, 34:337-342.

Cushman, Mark, et al, "Structural investigation and anti-HIV activities of high molecular weight ATA polymers", J Org Chem, 1992, 57:7241-7248.

Gonzalez, R. Gilberto, et al, "Fractionation and structural elucidation of the active components of aurintricarboxylic acid, a potent inhibitor of protein nucleic acid interactions", Biochimica et Biophysica Acta, 1979, 562:534-545.

Heisig, G.V. and W.M. Lauer, "ammonium salt of aurin tricarboxylic", Organic Syntheses, 1941, 1:54.

Jang, Jun Ho, et al, "Nociceptive sensitization by complement C5a and C3a in mouse", Pain, 2010, 148:343-352.

Lee, Moonhee, et al, "Selective inhibition of the membrane attack complex of complement by low molecular weight components of the aurin tricarboxylic acid synthetic complex", Neurobiology of Aging, 2012, 33:2237-2246.

Lee, Moonhee, et al, "Aurin tricarboxylic acid self-protects by inhibiting aberrant complement activation at the C3 convertase and C9 binding stages", Neurobiology of Aging, 2013, 34:1451-1461.

Lee, Moonhee, et al, "Inhibition of aberrant complement activation by a dimer of acetylsalicyclic acid", Neurobiology of Aging, 2015, 36:2748-2756.

Liang, De-Yong, et al, "The complement component C5a receptor mediates pain and inflammation in a postsurgical pain model", Pain, 2012, 153(2):366-372.

Owens, Michael R. and Stein Holme, "Aurin tricarboxylic acid inhibits adhesion of platelets to subendothelium", Thrombosis Research, 1996, 81(2):177-185.

Yancey, Kim B., et al, "Studies of human C5a as a mediator of inflammation in normal human skin", The Journal of Clinical Investigation, Inc., 1985, 75:486-495.

Chemoprophylaxis in Babesia argentina infection in cattle, Australia Veterinary Journal, vol. 45 (1969), Queensland Dep. Primary Ind., Anim. Res. Inst., Yeerongpilly, Australia, L. G. Newton et al., pp. 404-407.

Inhibition of aberrant complement activation by a dimer of acetylsalicylic acid, Neurobiology of Aging (2015), Kinsmen Laboratory of Neurological Research, Department of Psychiatry, University of Psychiatry, University of British Columbia, Vancouver, BC, Canada, Moonhee Lee et al., pp. 2748-2756.

Depsides and Depsidones as Inhibitors of HIV-1 Integrase: Discovery of Novel Inhibitors through 3D Database Searching, Journal of Medicinal Chemistry (1997), 40(6), pp. 942-951 CODEN: JMCMAR; ISSN: 0022-2623, Laboratories of Molecular Pharmacology and Medicinal Chemistry Division of Basic Sciences, National Cancer Institute, Nouri Neamati et al.

Methylenedisalicylic acid derivatives: New PTP1B inhibitors that confer resistance to diet-induced obesity, Bioorganic & Medicinal Chemistry Letters (2007), 17(10),pp. 2760-2764, Department of Chemistry and Institute of Molecular Cell Biology, Inha University, Incheon, 402-751, S. Korea, Suja Shreshtha et al.

Novel Small-Molecule Inhibitors of Anthrax Lethal Factor Identified by High-Throughput Screening, Journal of Medicinal Chemistry (2006), 49(17), pp. 5232-5244, Department of Veterinary Molecular Biology, Montana State University, Bozeman, MT, 59717, USA, Igor A. Schepetkin et al.

Structure-based identification of a potent inhibitor targeting Stp1-mediated virulence regulation in *Staphylococcus aureus*, Cell Chemical Biology (2016), 23(8), pp. 1002-1013 CODEN: CCBEBM; ISSN: 2451-9448, Key Lab of Chemical Genomics, School of Chemical Biology and Biotechnology, Shenzhen Graduate School, Peking University, Shenzhen, 518055, Peop. Rep. China, Weihao Zheng et al.

Identification of Non-Nucleoside DNA Synthesis Inhibitors of Vaccinia Virus by High-Throughput Screening, Journal of Medicinal Chemistry (2008), 51(20), pp. 6563-6570, Department of Microbiology, School of Dental Medicine, University of Pennsylvania, Philadelphia, PA, 19104, USA, Mihai Ciustea et al.

Novel Inhibitors of Dengue Virus Methyltransferase: Discovery by in Vitro-Driven Virtual Screening on a Desktop Computer Grid, Journal of Medicinal Chemistry (2010), 53(4), pp. 1483-1495, Swiss Institute of Bioinformatics and Biozentrum, University of Basel, Basel, CH-4056, Switz, Michael Podvinec et al.

Aurintricarboxylic acid inhibits endothelial activation, complement activation, and von Willebrand factor secretion in vitro and attenuates hyperacute rejection in an ex vivo model of pig-to-human pulmonary xenotransplantation; Hyun Kyung Kim; Ji-Eun Kim; Hyun Cho Wi; Sang Woo Lee; Ji Yeon Kim; Hee Jung Kang; Young Tae Kim; Xenotransplantation: 2008, vol. 15, Issue 4, pp. 246-256.

Hyperacute lung rejection in the pig-to-human model platelet receptor inhibitors synergistically modulate complement activation and lung injury; Steffe Pfeiffer et al., Transplantation: 2003—vol. 75, Issue 7, pp. 953-959.

\* cited by examiner

METHODS FOR TREATING AND PREVENTING NOCICEPTIVE PAIN

TECHNICAL FIELD

This invention pertains to methods for preventing and/or treating nociceptive pain.

BACKGROUND

Nociceptive pain results from stimulation of specialized free nerve endings called nociceptors. Nociceptors sense and respond to tissue damage, for example caused by physical stimulation, such as chemical, mechanical or thermal stimulation.

Methods for preventing and/or treating nociceptive pain are desirable.

SUMMARY

Aspects of the invention include methods of treating a condition resulting in nociceptive pain by administering to a mammal a therapeutically effective amount of a compound selected from the group consisting of diacetyl salicylic acid (DAS), aurin tricarboxylic acid (ATA), aurin quadracarboxylic acid (AQA), aurin hexacarboxylic acid (AHA), and a combination thereof. The compound may comprise DAS, ATA, AQA, AHA, and or combinations thereof. The condition being treated may be thermal burn, ultraviolet burn, surgical trauma, or post-operative pain. The compound (i.e., DAS, ATA, AQA or AHA) may be a formulated in a skin care preparation at a concentration of 0.1 to 100 mg/mL. The skin care preparation may be formulated as a spray, gel, cream, lotion, stick, ointment, scrub, soap bar, tonic, roll-on formulation, sunscreen, shampoo or mousse. The compound may be formulated in a pharmaceutical composition at a concentration of 0.001 to 100 mg/mL. The pharmaceutical composition may comprise a solution suitable for intradermal or subcutaneous administration.

BRIEF DESCRIPTION OF THE DRAWINGS

Drawings which show non-limiting embodiments of the invention:

FIGS. 6A and 6B are photographs illustrating the effect of an embodiment of the invention.

FIGS. 7A and 7B are photographs illustrating the effect of an embodiment of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

The term an "effective amount" as used herein refers to the amount of the active agent sufficient to elicit a desired biological response (or, equivalently, to inhibit an undesired biological response). As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses.

The term "mammal" refers to any mammalian species including without limitation mice, rats, rabbits, dogs, primates and, in particular, humans.

The term "prevent" and "preventing" as used herein refers to arrest, delay of onset (i.e., the period prior to clinical manifestation of a condition) and/or reduction of the risk of developing, or worsening of, nociceptive pain in a subject.

The term "subject" as used herein, refers to an individual to whom an agent is to be delivered, e.g., for prophylactic or therapeutic purposes. Preferred subjects are mammals, including humans and domesticated mammals.

The term "treat", "treating" and "treatment" as used herein refers to relief, reduction or alleviation of nociceptive pain in a subject.

Figure 1:
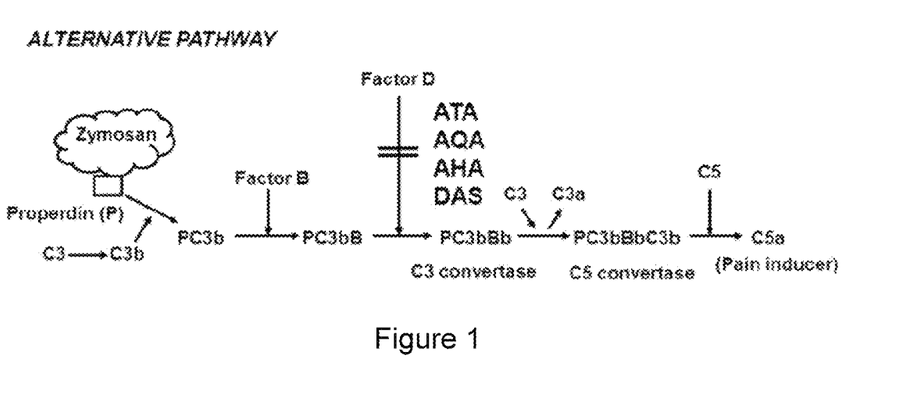
FIG. 1 is a diagram showing the alternative complement pathway, including blockade of the pathway according to an embodiment of the invention.
Figure 2A:
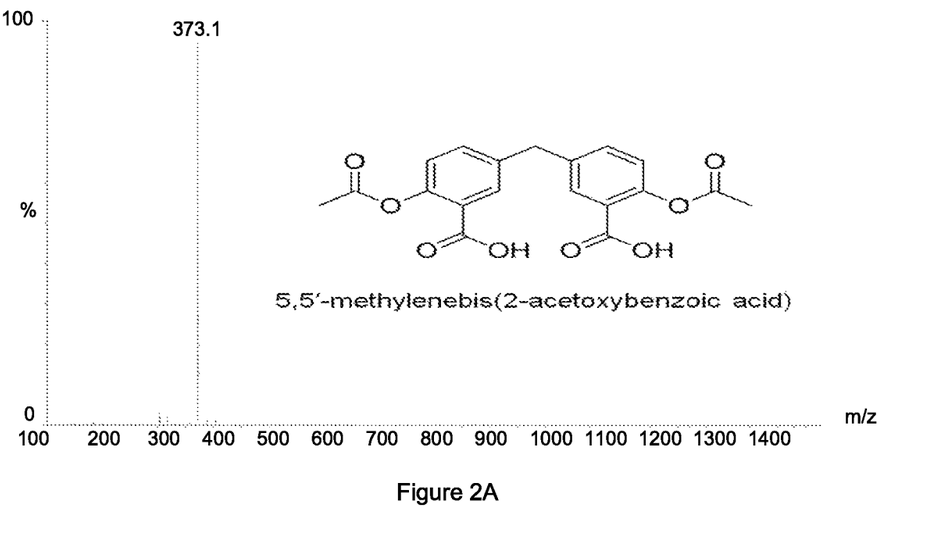
FIGS. 2A to 2D shows mass spectrographic results for purified DAS, ATA, AQA and AHA, respectively.
Figure 2B:
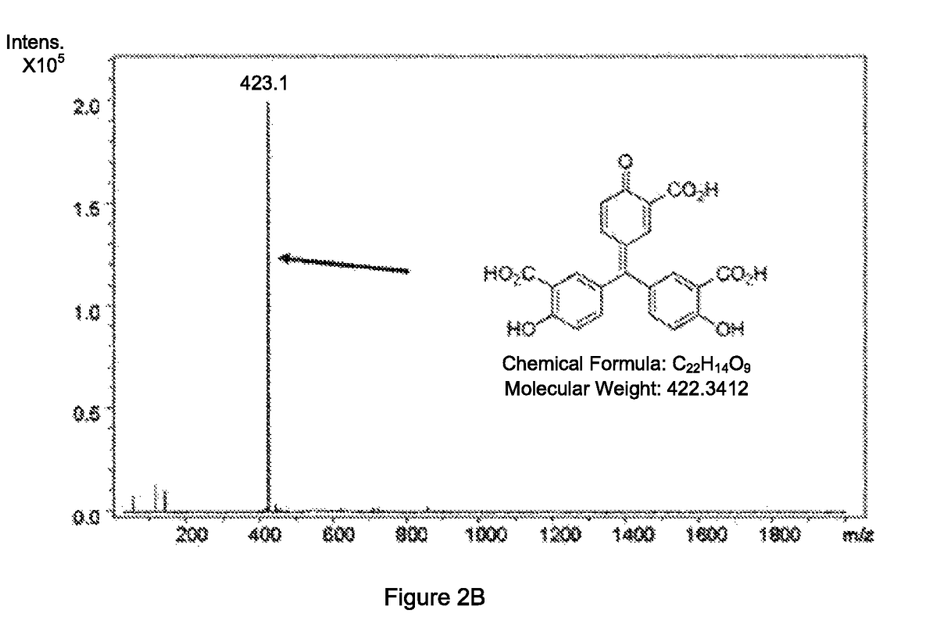
Figure 2C:
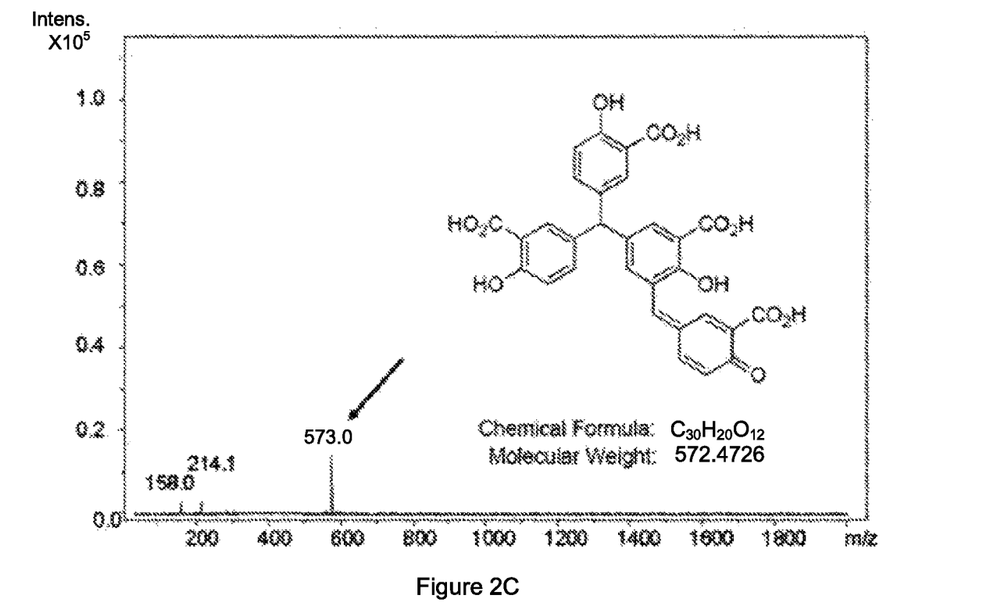
Figure 2D:
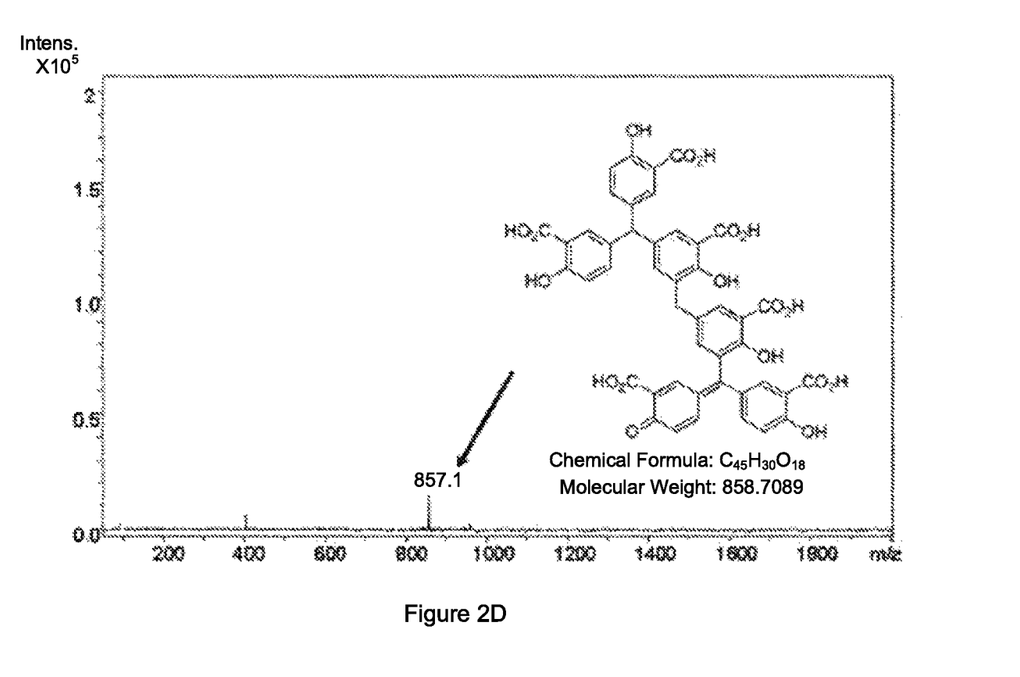

FIG. 1 shows the alternative complement pathway, as well as a mechanism by which embodiments of the present invention are believed to prevent and/or treat nociceptive pain. As shown in FIG. 1, C3 of the alternative complement pathway dissociates into C3a and C3b. The C3b fragment can then form a covalent amide or hydroxyl bond with cell surface proteins to form a bound complex. Factor B then attaches to the bound complex to form C3bB. Bound factor B can then be cleaved by the serum protease factor D to produce the highly active complex PC3bBb, known as C3 convertase. C3 convertase can bind additional C3b molecules to form PC3bBb3b, also known as C5 convertase. C5 convertase can cleave C5.

Without being bound by a particular theory, the inventors believe that nociceptive pain is generated by C5 cleavage by C5 convertase, which produces C5a. C5a acts upon C5a receptors, which are plentiful on peripheral neuronal nerve endings, including nociceptors. The inventors believe activation of C5a receptors leads to stimulation of nociceptors (e.g. A delta fibre nociceptors and C fibre nociceptors). Therefore blocking C5a production can block stimulation of nociceptors and thereby ameliorate nociceptive pain. As shown in FIG. 1, according to embodiments of the invention, factor D is bound to block C5a formation at the upstream, C3 convertase stage.

Aspects of the invention relate to methods of preventing and/or treating nociceptive pain by administration of 5,5'- methylenebis(2-acetoxybenzoic) acid (DAS), aurin tricarboxylic acid (ATA), aurin quadracarboxylic acid (AQA), aurin hexacarboxylic acid (AHA), and/or combinations thereof.

According to some embodiments, these compounds are administered in a concentration sufficient to inhibit factor D cleavage of C3B to prevent C5a formation.

According to some embodiments, these compounds are topically administered to patients with thermal or ultraviolet burns.

According to some embodiments, these compounds are topically administered to patients with post-surgical wounds or trauma requiring surgical intervention.

According to some embodiments, these compounds are topically administered to patients with any condition in which acute or chronic nociceptive pain accompanies aberrant complement activation.

According to some embodiments, one or more of these compounds may administered in the form of a skin care preparation, hair care preparation, or a pharmaceutical composition formulated for application to affected areas of the skin or scalp of a patient. Such preparations or compositions may for be formulated as a spray, gel, cream, lotion, stick, ointment, scrub, soap bar, tonic, roll-on formulation, sunscreen, or shampoo. The compounds may be provided in such preparations or compositions at a concentration of 0.001 to 100 mg/mL and may, for example, be topically applied one to five times daily. In some embodiments, one or more of compounds may be prepared as a solution suitable for injection intradermally or subcutaneously at similar concentrations and with similar frequency.

In some embodiments, one or more of the compounds may be dissolved at a concentration of 0.001 to 100 mg/mL, or 0.003 to 1 mg/mL, in water and applied as a spray or other means to the affected skin or scalp area. In some embodiments, one or more of compounds may be injected intradermally or subcutaneously at similar concentrations.

Aspects of the invention are based on properties of components of the aurin tricarboxylic acid synthetic complex of less than 1 kDa (ATAC). For many years it was assumed that aurin tricarboxylic acid was the product obtained by the classical synthetic method, originally described by Heisig and Lauer in 1941 (Heisig G B, Lauer M, 1941. Ammonium salt of aurin tricarboxylic acid. Organic Syntheses 1: 54), and in U.S. Pat. No. 4,007,270. However, it has been extensively documented since issuance of that patent in 1977 that this standard procedure, and variations of it, produce a complex of compounds, the majority of which are of high molecular weight and are of still uncertain structure (Cushman and Kanamathareddy, Synthesis of the covalent hydrate of the incorrectly assumed structure of aurintricarboxylic acid. Tetrahedron 46(5): 1491-1498, 1990; Gonzalez R C, Blackburn B J, Schleich T. 1979. Fractionation and structural elucidation of the active components of aurintricarboxylic acid, a potent inhibitor of protein nucleic acid interactions. Biochimica et Biophysica Acta 562: 534-545). These high molecular weight components have serious side effects. For example, they bind preferentially with proteins (Cushman M, Kananathareddy S, De Clercq E, Scols D, Goldman M E, Bowen J A. 1991. Synthesis and anti-HIV activities of low molecular weight aurintricarboxylic acid fragments and related compounds. J. Med. Chem 34: 337-342), especially those interacting with nucleic acids (Gonzalez et al., 1979). Embodiments of the invention circumvent these overwhelmingly detrimental problems by utilizing molecular weight components of the aurin tricarboxylic acid complex of less than 1 kDa.

In 1977, U.S. Pat. No. 4,007,270 was issued for "Complement Inhibitors" which included the term 'aurin tricarboxylic acid'. But the patent failed to show the true chemical nature of the material upon which the claims were based. There was no chemical or structural analysis of the patentee's synthetic product. Those skilled in the art would have concluded, based on subsequent publications that the 'aurin tricarboxylic acid', as described in that patent, was not the material claimed, and would therefore not be useful in the applications described. Firstly, they would have been taught, on the basis of molecular analyses conducted subsequently to issuance of U.S. Pat. No. 4,007,270, that the product, as produced by the synthetic method described in the patent, would not be aurin tricarboxylic acid, but would consist mostly of a mixture of high molecular weight materials of uncertain structure (e.g. Gonzalez et al., 1979, Cushman and Kanamatharedy, 1990). They would further have been taught that these components have powerful side effects which would render them unsuitable for human administration, including inhibition of protein nucleic acid interactions (Gonzales et al., 1979), and inhibition of adhesion of platelets to endothelium (Owens M R, Holme S. 1996. Aurin tricarboxylic acid inhibits adhesion of platelets to subendothelium. Thrombosis Res. 81: 177-185). They would also have been taught that the proposed mechanism of action was against the opsonizing components of complement as shown by the described effects on C1 inhibitor (Test Code 026) and not a specific inhibitor of the membrane attack complex, or of C3 convertase. Therefore, by inhibiting the essential function of classical pathway opsonization, the material would have been unsuitable for chronic administration.

The crude material as the starting point for ATAC can be obtained by synthesis using the method of Cushman and Kanamathareddy (Cushman and Kanamathareddy, 1990). It can also be prepared from commercial sources, such as the triammonium salt of the aurin tricarboxylic acid complex known as Aluminon, or as 'aurin tricarboxylic acid' from suppliers such as Sigma-Aldrich. The sources and methods of synthesis of these products have not been publicly described.

More than 85% of the powder the present inventors synthesized, or equivalent powder obtained from commercial sources including Aluminon, is a mixture of high molecular weight polymeric products. The exact structures of these products are as yet uncertain (Gonzales et al., 1979; Cushman and Kanamathareddy, 1990; Cushman M, Wang P, Stowell J G, Schols D, De Clercq E. 1992. Structural investigation and anti-HIV activities of high molecular weight ATA polymers. J. Org. Chem. 57: 7241-7248).

The powder the present inventors obtained from synthesis, or commercially purchased 'aurin tricarboxylic acid' from Sigma-Aldrich, or from Aluminon, was separated into high and low molecular weight components by passing through 1 kDa and 0.5 kDa MW filters. The low MW components were separated and analyzed by mass spectroscopy. Results from the three sources were almost identical. The low MW components made up only 12-16% of the total. They all contained three molecules of MW 422, 543, and 857. These MWs correspond to structures with three, four and six salicylic acid moieties. The present inventors refer to these as aurin tricarboxylic acid (ATA), aurin quadracarboxylic acid (AQA) and aurin hexacarboxylic acid (AHA). They were in a rough proportion of 78% ATA, 15% AQA and 7% AHA, or approximately 11%, 2%, and 1% of the crude starting material. This mixture is referred to as the aurin tricarboxylic acid complex (ATAC). In some embodiments, ATAC may be comprised of 60 to 90% AHA, 10 to 30% AQA, and 1 to 20% AHA.

The invention can be further understood by reference to the following examples, which are provided by way of illustration and are not meant to be limiting.

Example 1

Preparation of DAS, ATA, AQA and AHA

DAS can be synthesized in a pure form: see for example WO 2015/070354 and Lee et al. Neurobiol Aging 36 (2015), pp. 2748-2756, incorporated by reference herein.

The method for synthesizing ATAC has been described in detail for example in US 2015/0065573, incorporated by reference herein. ATA, AQA and AHA can be obtained from the complex by passing ATAC through a 1 kDa filter. Alternatively they can be obtained by dialysis through a 3 kDa membrane. In both cases they can then be separated into individual components on a GE Healthcare LH-20 size exclusion chromatography column packed in 60% ethanol.

FIGS. 2A to 2D show mass spectrographic results in the ES negative mode for purified DAS, ATA, AQA and AHA. In each case a single major peak was obtained corresponding to −1 of the theoretical molecular weight. These are DAS 372, ATA 422, AQA 543, and AHA 857. These data confirm that suitably purified products were being used to obtain the data reported in the further Examples below.

Example 2

Inhibition of C3B Cleavage

To investigate efficacy of DAS, ATA, AQA and AHA and to inhibit C3B cleavage in SH-SY5Y human neuroblastoma cells, a CH50 type analysis was performed. Lactate dehydrogenase (LDH) release from dead cells was the end point. Reaction mixtures were: SH-SY5Y cells ($10^5$ cells in 1 ml DMEM/F-12 medium), 250 μL of undiluted human serum and 250 μL of DAS (3 μM), ATA (5 μM), AQA (5 μM), or AHA (5 μM). Mixtures were incubated at 37° C. for 3 h. 100 μl of cell free reaction mixtures were transferred to 96 well plates where they were mixed with a solution containing 15 μl lactate (36 mg/ml in PBS) plus 15 μl p-iodonitrotetrazolium violet (INT, 2 mg/ml in PBS). The enzymatic reaction was started by the addition of 15 μl of $NAD^+$/diaphorase solution (3 mg/ml $NAD^+$; 2.3 mg solid/ml diaphorase). After 1 h, optical densities were measured with a Model 450 microplate reader (Bio-Rad Laboratories, Richmond, Calif.) using a 490-nm filter. The amount of LDH released was expressed as a percentage of the value obtained in comparative wells where cells were 100% lysed by 0.1% Triton X-100.

Figure 3:
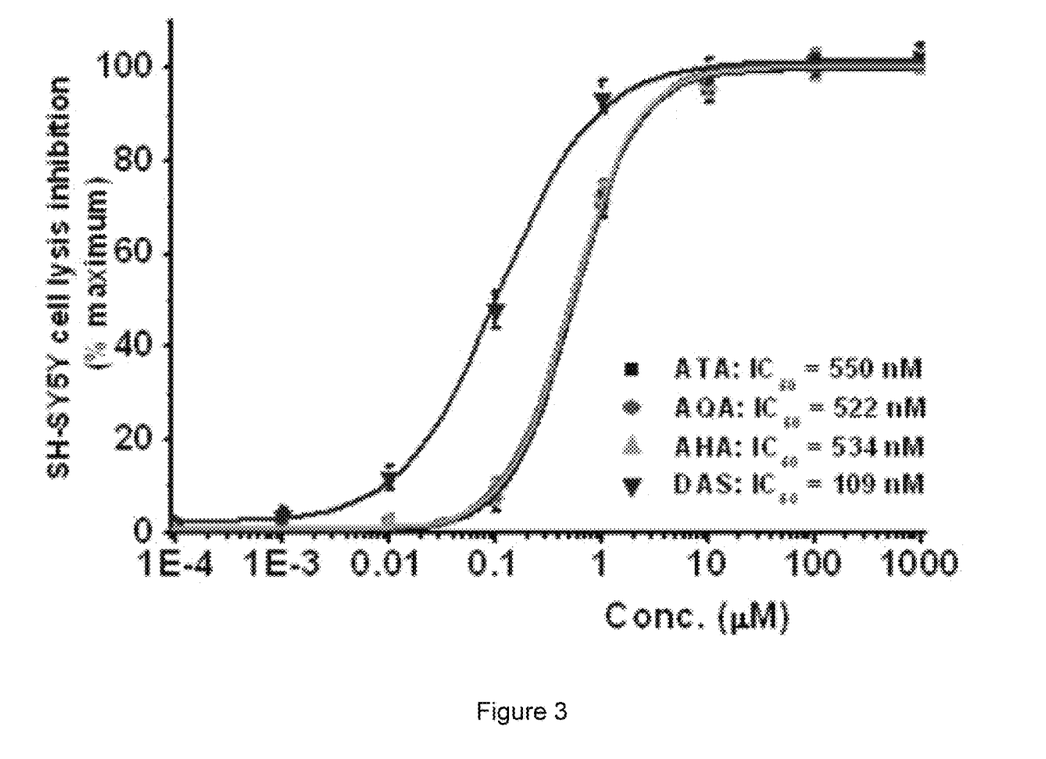
FIG. 3 is a graph showing inhibition of C3B cleavage in human neuroblastoma SH-SY5Y cells as a function of the concentration of DAS, ATA, AQA and AHA.

Results are shown in FIG. 3. Cell lysis was concentration dependent for each of the components investigated. The concentration to inhibit cell lysis by 50% (IC 50) was for DAS 109 nM; ATA 550 nM; AQA, 522 nM; and AHA, 534 nM. These results establish that the inhibitors were effective in inhibiting C3B cleavage in a concentration range suitable for administration to mammalian species in vivo.

Example 3

Blockade of C5a Formation

Figure 4:
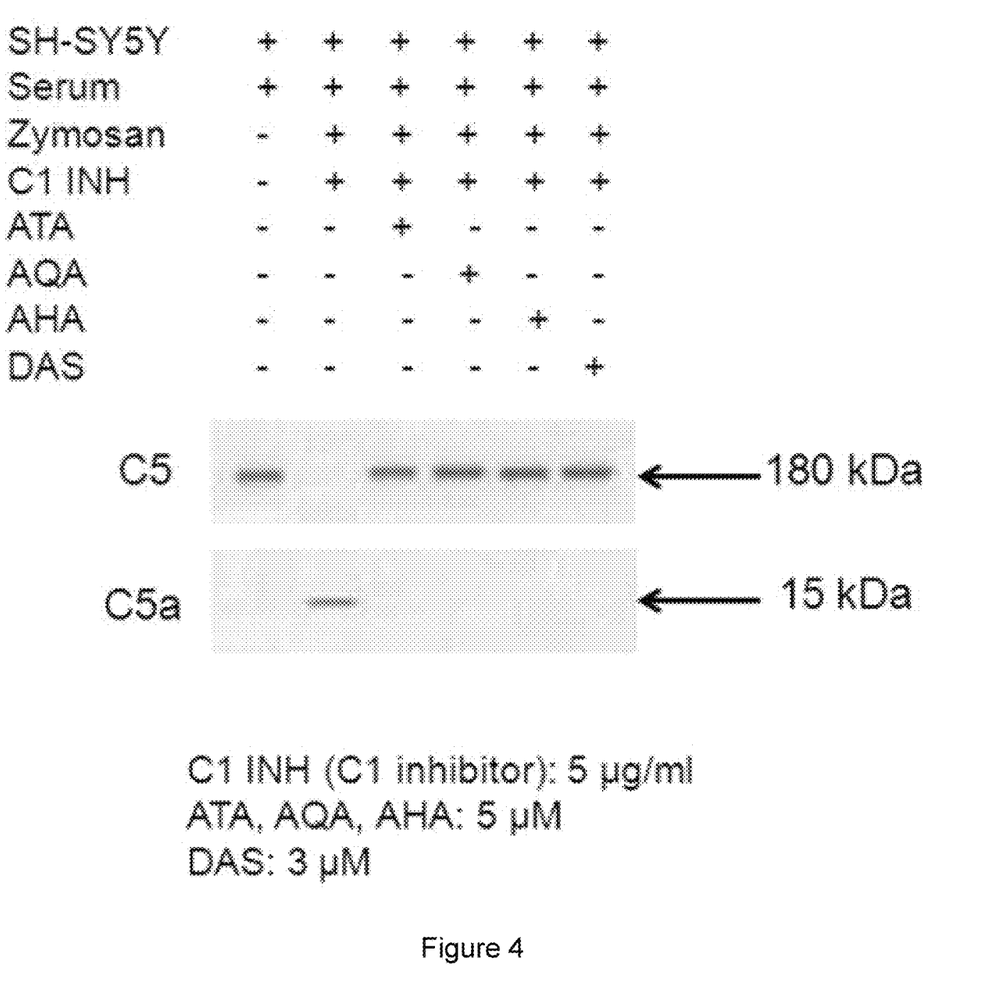
FIG. 4 is a western blot diagram showing blockade of C5a formation in human neuroblastoma SH-SY5Y cells by DAS, ATA, AQA and AHA.

To verify that each of the inhibitors was acting by inhibiting formation of C5 convertase, western blotting experiments were carried out. Results are shown in illustrated in FIG. 4. SH-SY5Y human neuroblastoma cells ($2\times10^5$ cells in 1 ml DMEM/F-12 medium including 10% human serum) were incubated with zymosan (100 μg/ml) in 24 well plates at 37° C. for 1 h with or without DAS (3 μM), ATA (5 μM), AQA (5 μM), or AHA (5 μM). To inhibit any classical pathway activation, C1 inhibitor (5 μg/ml) was added. Supernatants were obtained by centrifugation at 4000 g for 30 min through 30 K-filters (Amicon® Ultra-15, 30,000 NMWL, Millipore, Billerica, Mass.). The filtrates were dried and added to the loading buffer for SDS-PAGE (50-mM Tris (pH 6.8), 0.1% SDS, 0.1% bromophenol blue, and 10% glycerol). Proteins were separated in 10% polyacrylamide gels at 70V for 6 h. The proteins were then transferred to polyvinylidene difluoride (PVDF) membranes (Bio-Rad, CA) at 30 mA for 2 hours. After washing with PBS-T, the membranes were treated with a mouse monoclonal C5/C5a antibody (Abcam, Cambridge Mass., 1/2000) for 15 hours at 4° C. The membranes were then treated with an appropriate HRP-conjugated anti-mouse IgG (A3682, 1/3,000; Sigma) for 3 hours at room temperature. The bands were visualized with an enhanced chemiluminescent system and exposure to photographic film (Hyperfilm ECL; Amersham Pharmacia Biotech, Little Chalfont, UK). The upper panel shows the constituents added to each lane. The lower panel shows the corresponding western blot results. They show that in the absence of inhibitors, C5a was readily detected in the serum. However in the presence of each of the inhibitors, C5a was no longer formed.

Example 4

Thermal Burns

Figure 5:
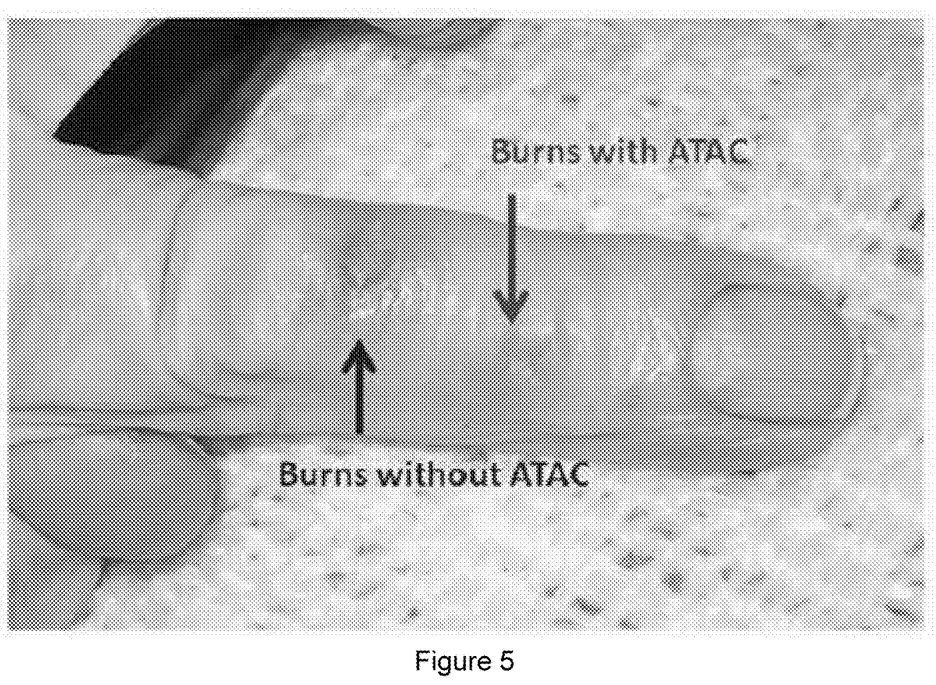
FIG. 5 is a photograph showing effects of treatment of thermal burns on a subject's finger with a control treatment and a test treatment according to an embodiment of the invention.

A 92 year female subject inadvertently burned her ring finger in two places on the range of a stove. The distal burn was sprayed with a water solution of 1 mg/mL ATAC (78% ATA, 15% AQA, and 7% AHA), while the proximal burn was untreated. The subject reported that the pain disappeared in the sprayed distal burn within a minute while pain persisted in the untreated proximal burn. The proximal burn developed a wheal that persisted for a month as shown in FIG. 5 while the distal burn did not develop a wheal.

Example 5

Thermal Burns

Figure 6A:
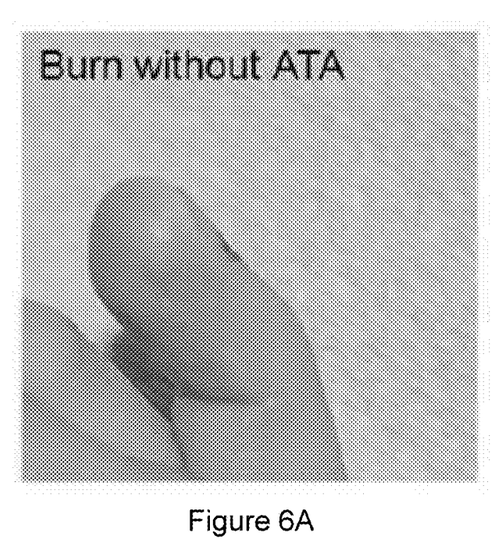
FIG. 6A shows effects of treatment of a thermal burn on a subject's finger at the time of injury.
Figure 6B:
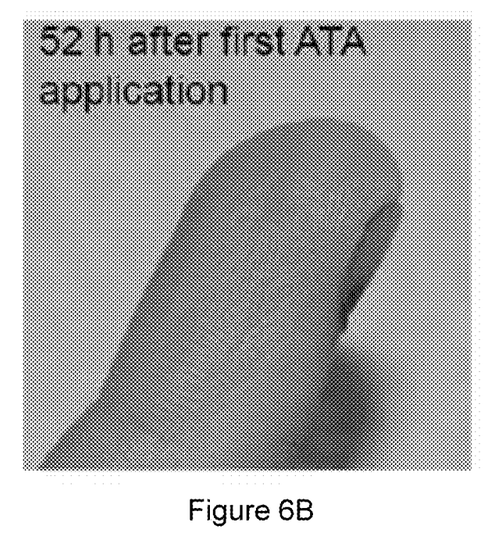
FIG. 6B shows the subject's finger 52 hours after treatment with a test treatment according to an embodiment of the invention.

A 12 year old male subject inadvertently burned his thumb on an oven grill. FIG. 6A shows a photograph of the thumb at around the time of injury. The thumb was subsequently sprayed with a water solution of 0.00625 mg/mL ATAC (78% ATA, 15% AQA, and 7% AHA). The subject reported that the pain disappeared within a minute of treatment. No wheal developed as shown by the photo taken 3 days later shown in FIG. 6B.

Example 6

Ultraviolet Burns

Figure 7A:
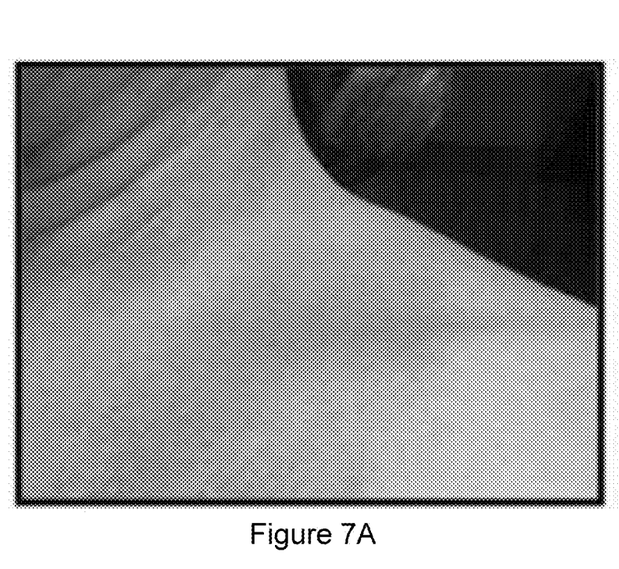
FIG. 7A shows a sunburn on a subject's shoulder that developed twelve hours after exposure to sunlight.
Figure 7B:
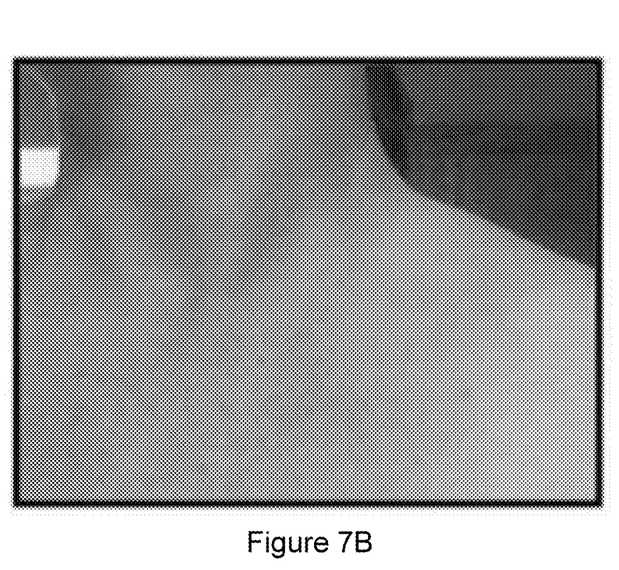
FIG. 7B shows the same area of the subject twelve further hours after application of a test treatment according to an embodiment of the invention.

A 50 year old fair-skinned female subject was overexposed to sunlight and 12 hours later developed a characteristic reddish sunburn on her left shoulder as shown in FIG. 7A. The subject applied water solution of 0.00625 mg/mL ATAC (78% ATA, 15% AQA, and 7% AHA) and an ointment of 0.0031 mg/mL ATAC (78% ATA, 15% AQA, and 7% AHA) in aloe vera gel. The subject reported that pain upon touching the sunburned area disappeared almost immediately after application of each treatment. Redness also diminished over the next several hours. FIG. 7B shows the sunburned area 12 hours later, showing that the sunburn redness had disappeared.

Prophetic Example 1

Thermal Burns

Topically apply a composition comprising a water solution of 0.00625 mg/mL to 1 mg/mL DAS to areas of thermal burns on a patient. Within minutes less pain is reported than would be reported for a control composition without DAS. Within hours less redness is reported than would be reported for a control composition without DAS.

Prophetic Example 2

Ultraviolet Burns

Topically apply a composition comprising 0.0031 mg/mL to 0.00625 mg/mL DAS (water solution or aloe vera gel based ointment) to areas of ultraviolet burns on a patient. Within minutes less pain is reported than would be reported for a control composition without DAS. Within hours less redness is reported than would be reported for a control composition without DAS. No wheal is reported, in contrast to a wheal that would be reported for a control composition without DAS.

This application is intended to cover any variations, uses, or adaptations of the invention using its general principles. Further, this application is intended to cover such departures from the present disclosure as come within known or customary practice in the art to which this invention pertains and which fall within the limits of the appended claims. Accordingly, the scope of the claims should not be limited by the preferred embodiments set forth in the description, but should be given the broadest interpretation consistent with the description as a whole.

The invention claimed is:

1. A method of treating a condition resulting in nociceptive pain by administering to a mammal a therapeutically effective amount of aurin tricarboxylic acid (ATA), wherein the method excludes administration of components of aurin tricarboxylic acid complex greater than or equal to 1 kDa, wherein the condition is surgical trauma or post-operative pain.

2. A method according to claim 1 wherein the condition is surgical trauma.

3. A method according to claim 1 wherein the condition is post-operative pain.

4. A method according to claim 1 wherein the ATA is formulated in a skin care preparation at a concentration of 0.001 to 1 mg/mL.

5. A method according to claim 4 wherein the skin care preparation is formulated as a spray, gel, cream, lotion, stick, ointment, scrub, soap bar, tonic, roll-on formulation, sunscreen, shampoo or mousse.

6. A method according to claim 1 wherein the ATA is formulated in a pharmaceutical composition at a concentration of 0.001 to 1 mg/mL.

7. A method according to claim 6 wherein the pharmaceutical composition comprises a solution suitable for intradermal or subcutaneous administration.

* * * * *